(12) United States Patent
Ma et al.

(10) Patent No.: US 11,304,898 B2
(45) Date of Patent: Apr. 19, 2022

(54) METHOD OF TREATING CARCINOMA

(71) Applicant: SUN PHARMA ADVANCED RESEARCH COMPANY LTD, Mumbai (IN)

(72) Inventors: Wen Wee Ma, Buffalo, NY (US); Alex Adjei, Saratoga, CA (US); Lynne Bui, Saratoga, CA (US); Ronald Harning, Cranbury, NJ (US); Ajay Khopade, Baroda (IN); Subhas Bhowmick, Baroda (IN); Natarajan Arulsudar, Kodichikkanahalli (IN); Narendra Lakkad, Mumbai (IN)

(73) Assignee: SUN PHARMA ADVANCED RESEARCH COMPANY LTD, Mumbai (IN)

( * ) Notice: Subject to any disclaimer, the term of this patent is extended or adjusted under 35 U.S.C. 154(b) by 264 days.

(21) Appl. No.: 15/580,732

(22) PCT Filed: Jun. 8, 2016

(86) PCT No.: PCT/IN2016/050175
§ 371 (c)(1),
(2) Date: Dec. 8, 2017

(87) PCT Pub. No.: WO2016/199169
PCT Pub. Date: Dec. 15, 2016

(65) Prior Publication Data
US 2018/0140549 A1    May 24, 2018

(30) Foreign Application Priority Data
Jun. 9, 2015  (IN) .................. 2207/MUM/2015

(51) Int. Cl.
| | | |
|---|---|---|
| *A61K 9/10* | (2006.01) |
| *A61K 31/337* | (2006.01) |
| *A61K 9/00* | (2006.01) |
| *A61K 9/51* | (2006.01) |
| *A61P 35/00* | (2006.01) |
| *A61K 47/10* | (2017.01) |
| *A61K 47/12* | (2006.01) |
| *A61K 47/28* | (2006.01) |
| *A61K 47/32* | (2006.01) |

(52) U.S. Cl.
CPC .............. *A61K 9/10* (2013.01); *A61K 9/0019* (2013.01); *A61K 9/5123* (2013.01); *A61K 9/5138* (2013.01); *A61K 9/5146* (2013.01); *A61K 31/337* (2013.01); *A61K 47/10* (2013.01); *A61K 47/12* (2013.01); *A61K 47/28* (2013.01); *A61K 47/32* (2013.01); *A61P 35/00* (2018.01)

(58) Field of Classification Search
CPC ...... A61K 9/10; A61K 9/5138; A61K 9/5146; A61K 9/5123; A61K 47/10; A61K 47/12; A61K 47/28; A61K 47/32; A61K 9/0019; A61K 31/337; A61P 35/00
See application file for complete search history.

(56) References Cited

U.S. PATENT DOCUMENTS

2010/0297244 A1* 11/2010 Khopade .............. A61K 9/1075
424/489
2013/0259922 A1* 10/2013 Haas .................... A61K 9/1272
424/450

FOREIGN PATENT DOCUMENTS

| WO | WO-2009087678 A2 | 7/2009 |
| WO | WO-2013044219 A1 | 3/2013 |

OTHER PUBLICATIONS

Jones (Phase II study of paclitaxel therapy for unresectable biliary tree carcinomas, J Clin Oncol. Aug.; 14(8):2306-10) (Year: 1996).*

(Continued)

*Primary Examiner* — Gollamudi S Kishore
(74) *Attorney, Agent, or Firm* — Blank Rome LLP

(57) ABSTRACT

A method of treating patients suffering from carcinoma of intrahepatic or extra hepatic bile duct or gall bladder which is locally advanced or metastatic, by intravenously administering to the patient, paclitaxel in the form of a nanodispersion. The nanodispersion comprises particles with a mean particle size less than 300 nm and is free of polyoxyethylated castor oil and free of a protein.

13 Claims, No Drawings

(56) References Cited

OTHER PUBLICATIONS

Tajima, H., etal in Oncology Leters, vol. 4, Issue 6, pp. 1281-1284, 2012.*
Ilkoo Noh et al.; Co-delivery of paclitaxel and gemcitabine via CD44-targeting nanocarriers as a prodrug with synergistic antitumor activity against human biliary cancer; Biomaterials., vol. 53, 2015, pp. 763-774.
Tae-You Kim et al.; Phase I and Pharmacokinetic Study of Genexol-PM, a Cremophor-Free, Polymeric Micelle-Formulated Paclitaxel, in Patients with Advanced Malignancies; Clinical Cancer Research, vol. 10, No. 11, Jun. 1, 2004 (Jun. 1, 2004), pp. 3708-3716.
T Hamaguchi et al.; A phase I and pharmacokinetic study of NKI05, a paclitaxel incorporating micellar nanoparticle formulation; British Journal of Cancer, vol. 97, No. 2, Jul. 2007 (Jul. 2007), pp. 170-176.
Keon UK et al.; Abstract 4659: Phase II study of a weekly liposomal paclitaxel formulation (Genexol®-PM) and gemcitabine® combination chemotherapy in patients with advanced biliary cancer; https://cancerres.aacrjournals.org/content/73/8_Supplement/4659 ; Clinical Trials; Proceedings: AACR 104th Annual Meeting 2013; Apr. 6-10, 2013.
Cancer Research, Apr. 2013, vol. 73, No. 8 Suppl., p. 1141-1142, Abstract No. 4659, doi: 10.1158/1538-7445.AM2013-4659 <URL:https://cancerres.aacrjournals.org/content/73/8_Supplement/4659.short>.
Gong, et al., Polymeric Micelles Drug Delivery System in Oncology, Journal of Controlled Released, 2012, 159:312-323.

\* cited by examiner

METHOD OF TREATING CARCINOMA

CROSS REFERENCE TO RELATED APPLICATIONS

This application is a National Stage of International Application No. PCT/IN2016/050175, filed Jun. 8, 2016, claiming priority based on Indian Patent Application No. 2207/MUM/2015, filed Jun. 9, 2015, the contents of all of which are incorporated herein by reference in their entirety.

FIELD OF INVENTION

The present invention relates to a method of treating a patient suffering from carcinoma of intrahepatic or extra hepatic bile duct or gall bladder which is locally advanced or metastatic, by intravenously administering therapeutically effective amount of paclitaxel or its pharmaceutically acceptable salt.

BACKGROUND OF THE INVENTION

Carcinoma of the bile duct is a rare disease and its treatment remains a major challenge for both surgeons and medical oncologists. The frequency of these tumours in various Western countries ranges from approximately 2 to 6 per 100000/year. Within the bile tract, tumours of the gallbladder are more frequent than tumours of the ductal system. Both tumour types occur preferentially in older patients, with a peak incidence in the fifth to seventh decade. Because of the lack of characteristic early symptoms, curative surgery is rare. Consequently, the course of the disease is usually rapid with a survival time of approximately 6 months. Death is mainly due to gastrointestinal haemorrhage, hepatic failure or progressive cachexia. For patients with locally advanced or metastatic disease, the role of chemotherapy remains a choice. There are few data in the literature concerning chemotherapy in patients with bile tract cancer. Most of these studies include small numbers of patients. 5-Fluorouracil (5-FU) and mitomycin-C (Mit-C) are among the most studied agents. Phase II studies have demonstrated that the achieved response rate with 5-FU is usually less than 20%. Mit-C, considered to be active against this disease, resulted in an objective response rate of 10% in an European Organization for Research and Treatment of Cancer (EORTC) study. Thus, there is an urgent need for new, active chemotherapeutic drug delivery system.

Previously, the present inventors had discovered a nanodispersion formed by diluting a solution of the anti-cancer drug like paclitaxel, water soluble polymer and surfactant system in a water miscible solvent, with an aqueous vehicle (U.S. Pat. No. 8,586,062 which has been incorporated herein by reference), was effective in treating solid tumors such as breast cancer. The inventors have found success in treating carcinoma of intrahepatic or extra hepatic bile duct or gall bladder which is locally advanced or metastatic by administering a nanodispersion of paclitaxel by intravenous infusion. The method is advantageous in that it is also effective in treating patients suffering from carcinoma of intrahepatic or extra hepatic bile duct or gall bladder which is locally advanced or metastatic who have failed in the first line of therapy with anti-cancer drugs such as gemcitabine, capecitabine and bevacizumab Mitomycin, 5-Fluorouracil, Cisplatin, Oxaliplatin, Leucovorin, Capecitabine, Bevacizumab, Etoposide, Gemcitabine, Divotinib, Cetuximab, Regorafenib, Carboplatin, Lupron, Casodex, Bleomycin, Pemetrexed, afinitor, sunitinib, Crizotinib or doxorubicin. Particularly, the method does not involve the administration of any premedication with corticosteroids. Also the method was effective in patients who had failed more than two lines of treatment with anti-cancer agents such as Mitomycin, 5-Fluorouracil, Cisplatin, Oxaliplatin, Leucovorin, Capecitabine, Bevacizumab, Etoposide, Gemcitabine, Divotinib, Cetuximab, Regorafenib, Carboplatin, Lupron, Casodex, Bleomycin, Pemetrexed, afinitor, sunitinib, Crizotinib or doxorubicin.

SUMMARY OF THE INVENTION

The present invention provides a method of treating patients suffering from carcinoma of intrahepatic or extra hepatic bile duct or gall bladder which is locally advanced or metastatic, said method comprising intravenously administering to the patient, paclitaxel in the form of a nanodispersion, said nanodispersion comprising particles with a mean particle size less than 300 nm, wherein the said nanodispersion is free of polyoxyethylated castor oil and is free of a protein.

DETAILED DESCRIPTION

The term 'intrahepatic bile duct cancer' as used herein means the cancers which develop in the smaller bile duct branches inside the liver.

The term 'extra-hepatic bile duct cancer' as used herein means either the perihilar cancers which develop at the hilum, where the left and right hepatic ducts have joined and are just leaving the liver or distal bile duct cancers. The perihilar cancers are also called Klatskin tumors. They are the most common type of bile duct cancer, accounting for more than half of all bile duct cancers. The Distal bile duct cancers are found further down the bile duct, closer to the small intestine. Like perihilar cancers, these are extrahepatic bile duct cancers because they start outside of the liver.

The American Joint Committee on Cancer (AJCC) TNM system has made a staging system which is a standard way for the cancer care team to sum up the extent of a cancer. The TNM system for all bile duct cancers contains 3 key pieces of information: T describes whether the main (primary) tumor has invaded through the wall of the bile duct and whether it has invaded other nearby organs or tissues, N describes whether the cancer spread to nearby (regional) lymph nodes (bean-sized collections of immune system cells throughout the body) and M indicates whether the cancer has metastasized (spread) to other organs of the body.

(The most common sites of bile duct cancer spread are the liver, peritoneum [the lining of the abdominal cavity] and the lungs). Numbers or letters appear after T, N, and M to provide more details about each of these factors. (http://www.cancer.org/cancer/bileductcancer/detailedguide/)

According to the method of the present invention, the patient suffering from carcinoma of intrahepatic or extra hepatic bile duct or gall bladder is locally advanced or metastatic.

The term 'locally advanced' refers to the cancer attaining a stage of $T_2$ or is more than $T_2$ or the N stage and the term 'metastatic cancer' refers to the cancer attaining the stage M.

The term "free of protein" means a composition that does not contain any protein. The proteins include those normally used in the art for drug stabilization such as albumin and the like.

According to the present invention, there is provided a method of treating patients suffering from carcinoma of intrahepatic or extra hepatic bile duct or gall bladder which is locally advanced or metastatic, said method comprising intravenously administering to the patient, paclitaxel in the form of a nanodispersion, said nanodispersion comprising particles with a mean particle size less than 300 nm, wherein the said nanodispersion is free of polyoxyethylated castor oil and is free of a protein. The nanodispersion used in accordance with the method may be prepared as per the description provided in U.S. Pat. No. 8,586,062 and U.S. Pat. No. 8,778,364 which are incorporated herein by reference. In one preferred embodiment, the nanodispersion comprising nanoparticles having a mean size less than 300 nm is dispersed in a vehicle comprising a water miscible solvent and water. In this embodiment the nanoparticles comprising a taxane derivative are selected from the group consisting of paclitaxel and docetaxel, a polymer and a surfactant comprising a mixture of fatty acids or its salts and sterol. In the preferred embodiment the fatty acid is caprylic acid and the sterol is selected from the group consisting of cholesteryl sulfate, cholesterol, sodium cholesteryl sulfate, sodium glychocholate, ursodeoxycholic acid, and dexamethasone. In another preferred embodiment the fatty acid is oleic acid and the sterol is cholesteryl sulfate. In yet another preferred embodiment the fatty acid is stearic acid and the sterol is cholesteryl sulfate.

In specific embodiment, the present invention provides a method of treating carcinoma of intrahepatic or extra hepatic bile duct or gall bladder which is locally advanced or metastatic in a human subject said method comprising preparing a nanodispersion comprising paclitaxel, a polymer selected from the group consisting of polyvinylpyrrolidone, polyglutamic acid or its salt and hyaluronic acid acid or its salt, a surfactant consisting of a mixture of caprylic acid or its salts and cholesteryl sulfate or its salt, and a water miscible solvent selected from the group consisting of alcohol, polyethylene glycol and polypropylene glycol by:
  a) forming a nanodispersion that remains stable for at least 4 hours with no aggregation or crystallization of the said drug by adding the drug solution to a sterile aqueous perfusion vehicle with mild agitation or shaking.
  b) delivery of the nanodispersion to the patient by intravenous infusion.

In one specific embodiment, the present invention provides a method of treating carcinoma of intrahepatic or extra hepatic bile duct or gall bladder which is locally advanced or metastatic wherein the method comprises administering paclitaxel for a three weekly cycle (21 day cycle) at a dose of 150 mg/m$^2$ to 300 mg/m$^2$ by intravenous infusion over 30 minutes wherein the paclitaxel is in the form a nanodispersion which is prepared by diluting a solution comprising paclitaxel, water soluble polymer, surfactant system in a water miscible solvent, in 5% dextrose solution.

According to the method of the present invention, the method of treatment involves intravenous administration of the nanodispersion of nanoparticles having a mean particle sized of less than 300 nms. In one embodiment, the invention provides a method of treating patients with carcinoma of intrahepatic or extra hepatic bile duct or gall bladder which is locally advanced or metastatic, comprising intravenous infusion of paclitaxel in the form of a nanodispersion comprising dispersed particles have a mean particle size less than 200 nm. In another embodiment the invention provides a method of treating patients with carcinoma of intrahepatic or extra hepatic bile duct or gall bladder which is locally advanced or metastatic, comprising intravenous infusion of paclitaxel in the form of a nanodispersion comprising dispersed particles have a mean particle size in the range of 50-150 nm. The nanodispersion can be either prepared by reconstituting a pre-concentrate solution or reconstituting the nanoparticles that are in the form of dry powder. When the nanodispersion is prepared using a pre-concentrate, it can be provided as a kit having two or more containers, for example two containers, wherein the first container contains paclitaxel, and a fatty acid and a sterol or salt thereof and optionally, a water soluble polymer and a water miscible non aqueous vehicle and the second container containing the aqueous vehicle. In another embodiment, the kit contains a first container having the nanoparticles in the form of dry powder and the second kit having the aqueous vehicle. In one embodiment, the solution is dried by freeze drying to obtain a lyophilisate.

In one specific embodiment, the reconstitution vehicle is 5% w/v dextrose injection which is isotonic. According to the method of the present invention, the intravenous administration is carried out over a period of 30 minutes using PVC or non-PVC IV set. The use of specialized DEHP-free solution containers or administration sets is not necessary to prepare or administer PICN infusions. It is recommended that all aseptic precautions are taken during reconstitution and intravenous administration as the nanodispersion is preservative free.

Depending upon the body surface area of the patient, the dose of paclitaxel is calculated. The volume of the pre-concetrate to be mixed with the aqueous vehicle like 5% dextrose is based on the dose of paclitaxel required. This in turn is based on the body surface area of the patient. In one instance, the height in cm and weight in kg of the patient is calculated and the BSA is determined using Mosterllar's formula: which is as follows: BSA (m$^2$)=([Height (cm)× Weight (kg)]/3600)$^{1/2}$. Depending upon the total dose required, number of the vials containing unit dose of paclitaxel is determined. In one specific embodiment, the paclitaxel concentration in the reconstituted nanodispersion is about 5 mg/mL. While preparing the reconstituted nanodispersion, the vial containing the pre-concentrate of the paclitaxel is flipped off and the surface is decontaminated with alcohol swab. 20 G needle is fixed onto the 5 cc luer lock syringe. Calculated amount of the preconcentrate of paclitaxel is withdrawn from counted number of vials, into the 5 mL luer lock syringe. The required volume of the preconcentrate is injected to 5% Dextrose bag holding the bag in the slanting position (an angle of approx. 45°). The preconcentrate is continued to be injected into infusion bag below upwards with continuous swirling movement of 5% Dextrose bag. Any re-flow from bag to syringe containing the preconcentrate is avoided. The bag is gently swirled after injecting the preconcentrate solution into it until dispersion is complete and no injection concentrate is visible at injection port. Care is taken to avoid generation of foam. If foaming occurs, the nanodispersion is made to stand for at least 15 minutes until foam subsides. The nanodispersion so formed is white translucent paclitaxel nanodispersion, homogenous without visible particulates and ready for infusion. If particulates or settling are visible, the infusion bag should be gently inverted again to ensure complete dispersion prior to use. The nanodispersion is to be discarded if precipitates are observed. Any unused portion is to be discarded. The infusion bag is mounted on the intravenous stand and the nanodispersion is infused and the rate is maintained such that it will be completed within 30 minutes.

According to the method of the present invention the nanodispersion may be administered in various dosing regimens. The nanodispersion may be administered either as a once weekly, once biweekly, once three weekly (21 day cycle) or once four weekly chemotherapeutic treatment regimen at various doses for different cancers including carcinoma of intrahepatic or extra hepatic bile duct or gall bladder which is locally advanced or metastatic. In one preferred embodiment of the method of the present invention the nanodispersion is administered once every 3 weeks ie as a 21 day cycle by intravenous infusion over 30 minutes wherein the paclitaxel is in the form a nanodispersion which is prepared by diluting a solution comprising paclitaxel, water soluble polymer, surfactant system in a water miscible solvent, in 5% dextrose solution.

In an alternative embodiment, the method includes the administration of the nanodispersion on days 1, 8 and 15 of a 21 day cycle. Alternatively, the method includes administration of the nanodispersion at days 1, 8 and 15 of each 28 day cycle. Thus, all variations in the dosage regimen of the paclitaxel nanodispersion as per the treatment duration are included within the scope of the invention. The patients continue to receive the method of treatment according to the present invention, until disease progression, development of unacceptable toxicities, non-compliance, intercurrent illness that prevents treatment continuation, withdrawal of consent, or change in subject condition that renders the subject unacceptable for further treatment. According to the method, in one embodiment, paclitaxel is administered weekly, for three weeks followed by a period of rest for one week, wherein it is administered at a dose range from 80 mg/m$^2$ to 175 mg/m$^2$ more preferably in the range of 95 mg/m$^2$ to 150 mg/m$^2$. In another embodiment of the method of the present invention, paclitaxel is administered once in two weeks, wherein it is administered at a dose range from 160 mg/m$^2$ to 300 mg/m$^2$. In a preferred embodiment, paclitaxel in the form of a nanodispersion used as per the method of the present invention is administered once in 21 day cycle (once three weekly) at a dose of 200 mg/m$^2$ to 325 mg/m$^2$, preferably 250 mg/m$^2$ to 300 mg/m$^2$ and most preferably 295 mg/m$^2$. For patients showing dose limiting toxicities, the dose is lowered from 295 mg/m$^2$ to 260 mg/m$^2$. In yet another embodiment, paclitaxel is administered once in four weeks, wherein it is administered at a dose range from 200 mg/m$^2$ to 325 mg/m$^2$.

In one embodiment, the patients suffering from carcinoma of intrahepatic or extra hepatic bile duct or gall bladder which is locally advanced or metastatic who had failed one or more prior lines of therapy with drugs such as gemcitabine, capecitabine or bevacizumab, were included in the study. In another embodiment the patients suffering from carcinoma of intrahepatic or extra hepatic bile duct or gall bladder which is locally advanced or metastatic and had failed more than two lines of treatment with anti-cancer agents such as Mitomycin, 5-Fluorouracil, Cisplatin, Oxaliplatin, Leucovorin, Capecitabine, Bevacizumab, Etoposide, Gemcitabine, Divotinib, Cetuximab, Regorafenib, Carboplatin, Lupron, Casodex, Bleomycin, Pemetrexed, afinitor, sunitinib, Crizotinib or doxorubicin were included in the study.

Further, those patients who had received prior chemotherapy as adjuvant therapy or for metastatic disease; or subjects who had received any chemotherapy (except palliative phosphate therapy for bone pain), major surgery, or irradiation were enrolled. Additionally, those patients who had completed chemotherapy at least 4 weeks prior to enrollment in the study (6 weeks for Mitomycin C or nitrosourea) or subjects were required to be free of any toxicities incurred as a result of the previous therapy.

The preliminary efficacy was measured by objective response rate (ORR) per RECIST v.1.1, in subjects with solid tumors, and, at the maximum therapeutic dose or highest dose evaluated, in an expansion cohort of subjects with carcinoma of intrahepatic or extra hepatic bile duct or gall bladder. Subjects were assessed for response with imaging studies to assess target and non-target lesions; unidimensionally for response at baseline and on Day 1 (±7 days) of Cycles 3, 5, 7, etc. The imaging method used for a given tumor at screening was consistently for that tumor throughout the study. Target lesion-response, non-lesion-response, and overall response analyses were based on site radiologist's evaluation of radiological and clinically detected lesions. Tumor response was categorized and evaluated according to RECIST Version 1.1. All measurable lesions up to a maximum of two lesions per organ and five lesions in total, representative of all involved organs, were identified as target lesions and recorded and measured at baseline. Target lesions were selected on the basis of their size (lesions with the longest diameter) and were representative of all involved organs, as well as their suitability for reproducible repeated measurements. All measurements were recorded in metric notation using calipers if clinically assessed. A sum of the diameters (longest for non-nodal lesions, short axis for nodal lesions) for all target lesions was calculated and reported as the baseline sum diameters, which was used as reference to further characterize any objective tumor regression in the measurable dimension of the disease. If lymph nodes were to be included in the sum, only the short axis was contributed. For the Non-target Lesions, all lesions (or sites of disease) not identified as target lesions, including pathological lymph nodes and all non-measurable lesions, were identified as non-target lesions and recorded at baseline. Measurements of these lesions were not required and they were followed as 'present', 'absent' or in rare cases, 'unequivocal progression'.

The patients continued to receive the method of treatment according to the present invention, until disease progression, development of unacceptable toxicities, non-compliance, intercurrent illness that prevents treatment continuation, withdrawal of consent, or change in subject condition that renders the subject unacceptable for further treatment.

In one embodiment, the specified volume of the preconcentrate solution comprising paclitaxel and a fatty acid and a sterol or salt thereof and the other optional components, like water soluble polymer and the non-aqueous, water miscible solvent is mixed with an aqueous vehicle such as 5% dextrose solution to achieve the nanodispersion that is used in the method of treatment of the present invention. While reconstituting, since paclitaxel is a cytotoxic drug, caution should be exercised in handling. The use of gloves is recommended. Spillage or leakage of nanodispersion used in the method of the present invention should be treated with dilute sodium hypochlorite (1% available chlorine) solution, preferably by soaking, and then water. If the preconcentrate or the nanodispersion contacts the skin, it is recommended to wash the skin immediately and thoroughly with soap and water. Given the possibility of extravasation, it is advisable to closely monitor the infusion site for possible infiltration during drug administration. The rate of infusion of the nanodispersion is less than 60, preferably 45 minutes or 30 minutes. This optimized reduced infusion time reduces the likelihood of infusion-related reactions. It is advantageously found that no premedication with corticosteroids to prevent hypersensitivity reactions is needed prior to the administration of nanodispersion of the present invention.

The nanodispersion used in the method according to an embodiment of the present invention comprises caprylic acid and cholesteryl sulfate. In one embodiment caprylic acid, also known as octanoic acid may be used in an amount ranging from about 0.001% w/v to about 5.0% w/v, more preferably from about 0.01% w/v to about 1.0% w/v and most preferably from about 0.01% w/v to about 0.5% w/v and cholesteryl sulfate is used in an amount ranging from about 0.001% w/v to about 5.0% w/v, more preferably from about 0.01% w/v to about 1.0% w/v and most preferably from about 0.01% w/v to about 0.5% w/v. It has been found surprisingly that this particular mixture of surfactants provides a nanodispersion of taxane derivatives that remains stable for more than 6 hours even at low ratios of lipid to taxane derivatives of about 1:5 to about 1:10.

Other embodiments according to the present invention use non-aqueous solvent which may be selected from the group consisting of alcohols, polyethylene glycols and/or mixtures thereof. In preferred embodiment of the present invention, a mixture of ethanol and PEG (polyethylene glycol) is used as the water miscible solvent. Ethanol is used in the nanodispersion composition of the present invention in an amount ranging from about 0.001% w/v to about 5% 10 w/v, more preferably from about 0.05% w/v to about 0.5% w/v and most preferably from about 0.1% w/v to about 0.25% w/v. Polyethylene glycols which are used preferably, include PEG-400 and PEG-3350. PEG-400 is used in the embodiments of the present invention in an amount ranging from about 0.01% w/v to about 20.0% w/v, more preferably from about 0.05% w/v to about 5.0% w/v and most preferably from about 1.0% w/v to about 2.5% w/v. PEG-3350 is used in the embodiments of the present invention in an amount ranging from 15 about 0.001% w/v to about 10.0% w/v, more preferably from about 0.05% w/v to about 5.0% w/v and most preferably from about 0.1% w/v to about 3% w/v.

In yet other embodiment a water soluble polymer suitable for the nanoparticles of the present invention is used. The examples of the water soluble polymers include, but are not limited to, polyvinylpyrrolidone, poloxomer, polyethylene glycol, polyvinyl alcohol, sodium alginate, sodium hyaluronate, gellna gum, carragenan, xanthan gum, dextran sulfate, chondroitin sulfate, pectinates, heparins, methacrylic acid copolymers, dermatan sulfate, cellulosic polymers such as sodium carboxymethyl cellulose, hydroxyethyl cellulose, hydroxypropyl methyl cellulose and the like and mixtures thereof. In the preferred embodiment polyvinylpyrrolidone is used as a water soluble polymer; According to one embodiment of the present invention, the amount of polyvinyl pyrrolidone used in the nanodispersion ranges from about 0.001% w/v. to about 20% w/v. The polymer is preferably used in an amount ranging from about 0.01% w/v to about 5.0% w/v. Most preferably, it is used in an amount ranging 20 from about 0.01% w/v to about 1.0% w/v.

The improvement in the method of treating carcinoma of intrahepatic or extra hepatic bile duct or gall bladder in a human patient by intravenously administering nanodispersion of paclitaxel encompasses all formulations prepared as described in the patent application U.S. Pat. No. 8,586, 062B2 or any other method known in the art.

While the present invention is disclosed generally above, additional aspects are further discussed and illustrated with reference to the examples below. However, the examples are presented merely to illustrate the invention and should not be considered as limitations thereto.

Example 1

The nanodispersion of paclitaxel of the present invention is prepared by the methods as described in examples 1 to 24 of U.S. Pat. No. 8,586,062B2.

Example 2-3

The nanodispersion used according to the method of the present invention, can also be prepared as the composition given below in Table 1.

TABLE 1

| | Composition details | | |
|---|---|---|---|
| Ingredient | Example 2 Quantity in mg/gm | Example 3 | % by weight |
| Paclitaxel | 100 | 100 | 10 |
| Polyethylene glycol -400 | 701.7 | 701.7 | 70.2 |
| Dehydrated alcohol/Ethanol | 100 | 100 | 10 |
| Butyric acid | 8.33 | — | 0.83 |
| Hexanoic acid | — | 8.33 | 0.83 |
| Sodium cholesteryl sulphate | 6.67 | 6.67 | 0.67 |
| Povidone K-12 | 83.3 | 83.3 | 8.33 |

Example 4

Patients having bile duct cancer were included in the study. The patients suffering from carcinoma of intrahepatic or extra hepatic bile duct or gall bladder which is locally advanced or metastatic that is 'patients with cancer attaining a stage of $T_2$ or is more than $T_2$ or the N stage and or stage M, were enrolled in the clinical trial. The patients who had failed at least one prior line of chemotherapy or two or more than two lines of chemotherapy were included in the clinical trial. The prior chemotherapy included administration of gemcitabine, capecitabine, Bevacizumab leucovorin, as Mitomycin, 5-Fluorouracil, Cisplatin, Oxaliplatin, Leucovorin, Etoposide, Divotinib, Cetuximab, Regorafenib, Carboplatin, Lupron, Casodex, Bleomycin, Pemetrexed, afinitor, sunitinib, Crizotinib or doxorubicin.

Further, those patients who had received prior chemotherapy as adjuvant therapy or for metastatic disease; or subjects who had received any chemotherapy (except palliative phosphate therapy for bone pain), major surgery, or irradiation are enrolled. Additionally, those patients who had completed chemotherapy at least 4 weeks prior to enrollment in the study (6 weeks for Mitomycin C or nitrosourea) or subjects were required to be free of any toxicity incurred as a result of the previous therapy were included. The patients continued to receive the method of treatment according to the present invention, until disease progression, development of unacceptable toxicities, non-compliance, intercurrent illness that prevents treatment continuation, withdrawal of consent, or change in subject condition that renders the subject unacceptable for further treatment.

The criteria for evaluating response was based on the protocol given as per RECIST v.1.1. The preliminary efficacy was measured by objective response rate (ORR) per RECIST v.1.1, in subjects with solid tumors, and, at the maximum therapeutic dose or highest dose evaluated, in an expansion cohort of subjects with carcinoma of intrahepatic or extra hepatic bile duct or gall bladder. Subjects were assessed for response with imaging studies to assess target and non-target lesions; unidimensionally for response at baseline and on Day 1 (±7 days) of Cycles 3, 5, 7, etc. The imaging method used for a given tumor at screening was kept consistent for that tumor throughout the study. Target lesion-response, non-target lesion-response, and overall response analysis was based on site radiologists evaluation of radiologically and clinically detected lesions. Tumor response was categorized and evaluated according to RECIST Version 1.1.

The evaluation of target lesions was done by assessing all measurable lesions of carcinoma of intrahepatic and extra-hepatic bile duct or gall bladder having upto a maximum of five lesions total and (a maximum of two lesions per organ) which were representative of all involved organs. Target lesions were selected on the basis of their size (lesions with the longest diameter) and were representative of all involved organs, as well as their suitability for reproducible repeated measurements. All measurements were recorded in metric notation using calipers if clinically assessed. A sum of the diameters (longest for non-nodal lesions, short axis for nodal lesions) for all target lesions was s calculated and reported as the baseline sum diameters, which was be used as reference to further characterize any objective tumor regression in the measurable dimension of the disease. When lymph nodes were included in the sum, only the short axis contributed.

The evaluation of non-target lesions was done to assess the lesions of carcinoma of intrahepatic and extrahepatic bile duct or gall bladder which are either locally advanced or at metastatic stage. It was done by assessing all lesions (or sites of disease) not identified as target lesions, including pathological lymph nodes and all non-measurable lesions, recorded at baseline. Measurements of these lesions was not required and they were followed as 'present', 'absent' or in rare cases, 'unequivocal progression'.

A total of 24 subjects suffering from carcinoma of intra-hepatic or extra hepatic bile duct or gall bladder which is locally advanced or metastatic and who had failed at least one prior line of chemotherapy or two or more than two lines of chemotherapy were enrolled in the trial. Four patients out of twenty four dropped out of the trial due to screening failure. The subjects were exposed to a dose of 295 mg/m$^2$ paclitaxel nanodispersion. Out of 20 patients, two withdrew consent for proceeding with the study. Each patient of the remaining 18 patients was treated in a 21 day cycle and the treatment continued till the patient responded either with a partial response, complete response or stable disease. Of the 18 patients one did not tolerate a dose of 295 mg/m$^2$ and one more patient was switched after 6 cycles of treatment to a dose of 260 mg/m$^2$. The results for the 18 patients are tabulated below in Table 2.

TABLE 2

| Patient (N = 18) demographics, prior chemotherapy and response | | | | | |
|---|---|---|---|---|---|
| Patient no | Stage | Metastatic Stage** | Prior chemotherapy | Dose administered | Best Overall Response |
| Patients showing partial response (4/18 = 22.2%) | | | | | |
| 1 | Advanced Biliary Tract Cancer (Type: Cholangiocarcinoma, with 2 metastatic sites the lymph nodes and invasion into the liver) | $M_2$ | none | 295 mg/m$^2$ | Partial Response* |
| 2 | Advanced Biliary Tract Cancer (Type: Cholangiocarcinoma, with 3 metastatic sites the lung, coeliac region nodes and invasion into the liver) | $M_3$ | Gemcitabine + Capecitabine | 295 mg/m$^2$ | Partial Response |
| 3 | Advanced Biliary Tract Cancer (Type: Cholangiocarcinoma, with 1 metastatic site, Abdominal Lymph Node) | $M_1$ | Capecitabine + Divotinib + Gemcitabine | 295 mg/m$^2$ | Partial Response |
| 4 | Advanced Biliary Tract Cancer (Type: Cholangiocarcinoma, with 4 metastatic sites, Left paratracheal lymph node/Right Paraaortic lymph node/Medial Liver lesion/Inferior Right Liver Lesion) | $M_4$ | Therapy 1: Gemcitabine Therapy 2: Cisplatin | 295 mg/m$^2$ | Partial Response |
| Patients showing stable disease (7/18 = 38.9%) | | | | | |
| 1 | Advanced Biliary Tract Cancer (Type: Adenocarcinoma of Gall bladder and extra hepatic bile ducts, with 1 metastatic sites, Liver) | $M_1$ | Gemcitabine + Cisplatin | 295 mg/m$^2$ | Subject ongoing in study, shows stable disease until Cycle 12 |
| 2 | Advanced Biliary Tract Cancer (Type: Intrahepatic Cholangiocarcinoma, with 2 metastatic sites portocaval and retroperitoneal lymph nodes and local invasion into the liver) | $M_2$ | Capecitabine + Divotinib + Gemcitabine | 295 mg/m$^2$ | Stable Disease* |
| 3 | Advanced Biliary Tract Cancer (Type: Intrahepatic Cholangiocarcinoma, with 1 metastatic site the peritoneum) | $M_2$ | Gemcitabine + Cisplatin | 295 mg/m$^2$ | Stable Disease |
| 4 | Advanced Biliary Tract Cancer (Type: Cholangiocarcinoma, with 2 metastatic sites the lymph nodes and invasion into the liver) | $M_2$ | Capecitabine + Gemcitabine | 295 mg/m$^2$ | Stable Disease |
| 5 | Advanced Biliary Tract Cancer (Type: Cholangiocarcinoma, with 1 metastatic site, invasion into the liver) | $M_1$ | Gemcitabine + Capecitabine | 295 mg/m$^2$ | Stable Disease |
| 6 | Advanced Biliary Tract Cancer (Type: Adenocarcinoma of Ampulla of Vater, with 2 metastatic sites, Liver/Abdominal wall mass) | $M_2$ | Therapy 1: 5-FU Therapy 2: Gemcitabine Therapy 3: Gemcitabine + Cisplatin | 295 mg/m$^2$ (Subject had dose reduction to 260 mg/m$^2$ in cycle 6) | Stable Disease |

TABLE 2-continued

Patient (N = 18) demographics, prior chemotherapy and response

| Patient no | Stage | Metastatic Stage** | Prior chemotherapy | Dose administered | Best Overall Response |
|---|---|---|---|---|---|
| 7 | Advanced Biliary Tract Cancer (Type: Cholangiocarcinoma, with 2 metastatic sites, Bone/Liver) | $M_2$ | Therapy 1: Gemcitabine + Cisplatin Therapy 2: Oxaliplatin + Folinic acid + 5FU | 295 mg/m$^2$ | Stable Disease |
| Patients showing progressive disease (7/18 = 38.9%) | | | | | |
| 1 | Advanced Biliary Tract Cancer (Type: Cholangiocarcinoma, with 2 metastatic sites, Liver/Lung) | $M_2$ | Therapy 1: Gemcitabine Therapy 2: Cisplatin | 295 mg/m$^2$ | Progressive disease* |
| 2 | Advanced Biliary Tract Cancer (Type: Cholangiocarcinoma, with 2 metastatic sites, Lymph Node/Jejunum) | $M_2$ | Gemcitabine + Cisplatin | 295 mg/m$^2$ | Progressive Disease |
| 3 | Advanced Biliary Tract Cancer (Type: Cholangiocarcinoma, with 1 metastatic site) | $M_1$ | Therapy 1: Gemcitabine + Cisplatin Therapy 2: Capecitabine + Oxaliplatin | 295 mg/m$^2$ | Progressive Disease |
| 4 | Advanced Biliary Tract Cancer (Type: Adenocarcinoma, with 3 metastatic sites, Lymph Nodes/Lungs/Peritoneum) | $M_3$ | Therapy 1: Gemcitabine Therapy 2: Cisplatin | 295 mg/m$^2$ | Progressive Disease |
| 5 | Advanced Biliary Tract Cancer (Type: Adenocarcinoma, with 3 metastatic sites, Peritoneal/Lymph node/Duodenum) | $M_3$ | Therapy 1: Gemcitabine + Cisplatin Therapy 2: Capecitabine + Cisplatin Therapy: Cisplatin | 260 mg/m$^2$ | Progressive Disease |
| 6 | Advanced Biliary Tract Cancer (Type: Cholangiocarcinoma, with 1 metastatic site, Liver) | $M_1$ | Gemcitabine + Cisplatin | 295 mg/m$^2$ | Progressive Disease |
| 7 | Advanced Biliary Tract Cancer (Type: Adenocarcinoma of Gall bladder with 2 metastatic site, Omentum/Peritoneum) | $M_2$ | Gemcitabine + Cisplatin | 295 mg/m$^2$ | Progressive Disease |

*A partial response, stable disease and progressive disease is as defined by RECIST Version 1.1
**$M_1$ refers to one metastatic site, $M_2$ refers to two metastatic sites, $M_3$ refers to three metastatic sites and $M_4$ refers to four metastatic sites.

The table indicates that 22.2% of the patients (4 of 18) showed partial response and 38.9% of the patients (7 of 18) showed stable disease and thus 11 of 18 patients or 61.1% of the patients who previously failed on one or more lines of chemotherapy benefited from the method of treatment of the present invention involving the administration of paclitaxel nanodispersion.

The invention claimed is:

1. A method of treating a patient suffering from carcinoma of intrahepatic or extra hepatic bile duct or gall bladder which is metastatic, said method comprising intravenously administering to the patient, paclitaxel in the form of a nanodispersion,
   wherein said nanodispersion comprises
   (a) particles comprising (i) paclitaxel, (ii) a water soluble polymer, and (iii) a surfactant comprising a mixture of a fatty acid or a salt thereof and a sterol or a salt thereof, the particles having a mean particle size less than 300 nm, and
   (b) a water miscible solvent, wherein the nanodispersion is free of polyoxyethylated castor oil and is free of any protein, and
   wherein the paclitaxel is administered once in a 21 day cycle at a dose of 295 mg/m$^2$.

2. The method as claimed in claim 1, wherein the method does not involve premedication with any corticosteroids.

3. The method as claimed in claim 1, wherein the patient suffering from carcinoma of intrahepatic or extra hepatic bile duct or gall bladder which is metastatic has failed to respond to one or more lines of treatment with one or more anti-cancer agents selected from mitomycin, 5-fluorouracil, cisplatin, oxaliplatin, leucovorin, capecitabine, bevacizumab, etoposide, gemcitabine, divotinib, cetuximab, regorafenib, carboplatin, lupron, casodex, bleomycin, pemetrexed, everolimus, sunitinib, crizotinib or doxorubicin.

4. The method as claimed in claim 1, wherein the patient suffering from carcinoma of intrahepatic or extra hepatic bile duct or gall bladder which is metastatic has failed more than two lines of treatment with anti-cancer agents.

5. The method as claimed in claim 4, wherein the lines of treatment that have failed include two or more of treatments with one or more anti-cancer agents selected from mitomycin, 5-fluorouracil, cisplatin, oxaliplatin, leucovorin, capecitabine, bevacizumab, etoposide, gemcitabine, divotinib, cetuximab, regorafenib, carboplatin, lupron, casodex, bleomycin, pemetrexed, everolimus, sunitinib, crizotinib or doxorubicin.

6. The method as claimed in claim 1, wherein the method comprises:
   a) preparing a solution comprising paclitaxel, a water soluble polymer, a surfactant and a water miscible solvent,
   b) preparing a nanodispersion that remains stable for at least 4 hours with no aggregation or crystallization of the said drug by adding the solution to a sterile aqueous perfusion vehicle with mild agitation or shaking, and
   c) intravenously administering the nanodispersion to the patient.

7. The method as claimed in claim 6, wherein the water soluble polymer is selected from the group consisting of polyvinylpyrrolidone, polyglutamic acid or its salt and hyaluronic acid or its salt, the surfactant consists of a mixture of sterol or its salts and fatty acid or its salts and the water miscible solvent is selected from the group consisting of alcohol, polyethylene glycol, polypropylene glycol and mixtures thereof.

8. The method as claimed in claim 1, wherein the nanodispersion comprises
   (a) a polymer selected from the group consisting of polyvinylpyrrolidone, polyglutamic acid or its salts and hyaluronic acid or its salts,
   (b) a surfactant consisting of a mixture of caprylic acid or its salts and cholesteryl sulphate or cholesterol acid salts, and
   (c) a water miscible solvent selected from the group consisting of alcohol, polyethylene glycol, polypropylene glycol and mixtures thereof.

9. The method as claimed in claim 1, wherein the water soluble polymer is selected from the group consisting of polyvinylpyrrolidone, polyglutamic acid or its salts and hyaluronic acid or its salts; the fatty acid is selected from the group consisting of caprylic acid, oleic acid and stearic acid; the sterol is selected from the group consisting of cholesteryl sulfate, cholesterol, sodium cholesteryl sulfate, sodium glychocholate and ursodeoxycholic acid; and the water miscible solvent is selected from the group consisting of alcohol, polyethylene glycol, polypropylene glycol and mixtures thereof.

10. A method of treating a patient suffering from metastatic carcinoma of the intrahepatic or extra hepatic bile duct or gall bladder who has failed to respond to one or more lines of treatment with one or more anti-cancer agents selected from mitomycin, 5-fluorouracil, cisplatin, oxaliplatin, leucovorin, capecitabine, bevacizumab, etoposide, gemcitabine, divotinib, cetuximab, regorafenib, carboplatin, lupron, casodex, bleomycin, pemetrexed, everolimus, sunitinib, crizotinib and doxorubicin, the method comprising intravenously administering to the patient paclitaxel at a dose of 295 mg/m$^2$ in the form of a nanodispersion once in a 21 day cycle, wherein the nanodispersion comprises
   (a) particles comprising (i) paclitaxel, (ii) a water soluble polymer, and (iii) a surfactant comprising a mixture of a fatty acid or a salt thereof and a sterol or a salt thereof, the particles having a mean particle size less than 300 nm, and
   (b) a water miscible solvent.

11. The method of claim 10, wherein the carcinoma is unresectable.

12. The method of claim 1, wherein the carcinoma is unresectable.

13. A method of treating a patient suffering from adenocarcinoma of intrahepatic or extra hepatic bile duct or gall bladder which is (a) unresectable and (b) locally advanced or metastatic, said method comprising intravenously administering to the patient, paclitaxel in the form of a nanodispersion,
   wherein the paclitaxel is administered once in a 21 day cycle at a dose of 295 mg/m$^2$,
   wherein said nanodispersion comprises
   (a) particles comprising (i) paclitaxel, (ii) a water soluble polymer, and (iii) a surfactant comprising a mixture of a fatty acid or a salt thereof and a sterol or a salt thereof, the particles having a mean particle size less than 300 nm, and
   (b) a water miscible solvent, wherein the nanodispersion is free of polyoxyethylated castor oil and is free of any protein.

\* \* \* \* \*